(12) United States Patent
Corcoran

(10) Patent No.: US 7,532,326 B2
(45) Date of Patent: May 12, 2009

(54) MULTIPLE-LABEL FLUORESCENCE IMAGING USING EXCITATION-EMISSION MATRICES

(76) Inventor: Timothy C. Corcoran, 127 Arlington Dr., Claremont, CA (US) 91711

( * ) Notice: Subject to any disclaimer, the term of this patent is extended or adjusted under 35 U.S.C. 154(b) by 249 days.

(21) Appl. No.: 11/175,955

(22) Filed: Jul. 6, 2005

(65) Prior Publication Data

US 2006/0007439 A1    Jan. 12, 2006

Related U.S. Application Data

(60) Provisional application No. 60/586,435, filed on Jul. 7, 2004.

(51) Int. Cl.
G01J 3/12    (2006.01)
(52) U.S. Cl. .................... 356/332; 356/300; 356/317
(58) Field of Classification Search .......... 356/317–318
See application file for complete search history.

(56) References Cited

U.S. PATENT DOCUMENTS

| | | | |
|---|---|---|---|
| 5,379,065 A | 1/1995 | Cutts | |
| 5,459,325 A | 10/1995 | Hueton et al. | |
| 5,631,734 A | 5/1997 | Stern et al. | |
| 5,776,782 A * | 7/1998 | Tsuji | 436/171 |
| 6,160,618 A * | 12/2000 | Garner | 356/318 |
| 6,172,785 B1 | 1/2001 | Wulf | |
| 6,211,989 B1 | 4/2001 | Wulf et al. | |
| 6,245,507 B1 | 6/2001 | Bogdanov | |
| 6,323,944 B1 | 11/2001 | Xiao | |
| 6,337,472 B1 | 1/2002 | Garner et al. | |
| 6,373,568 B1 | 4/2002 | Miller et al. | |
| 6,427,126 B1 | 7/2002 | Dabiri et al. | |
| 6,441,892 B2 | 8/2002 | Xiao | |
| 6,490,075 B1 | 12/2002 | Scheps et al. | |
| 6,495,363 B2 | 12/2002 | Bogdanov | |
| 6,495,818 B1 | 12/2002 | Mao | |
| 6,597,932 B2 | 7/2003 | Tian et al. | |
| 6,690,466 B2 | 2/2004 | Miller et al. | |
| 6,690,472 B2 * | 2/2004 | Kulp et al. | 356/437 |

(Continued)

OTHER PUBLICATIONS

Warner et al., "Quantitative Analyses of Multicomponent Fluorescence Data by Methods of Least Squares . . . ," Analytical Chemistry, vol. 49, No. 14, Dec. 1977.
Warner et al., "Analysis of Multicomponent Fluorescence Data," Analytical Chemistry, vol. 49, No. 4, Apr. 1977.
O'Brien et al., "ASTRAL, a hyperspectral imaging DNA sequencer," Review of Scientific Instruments, vol. 69, No. 5, pp. 2141-2146, May 1998.

(Continued)

Primary Examiner—Roy M Punnoose
Assistant Examiner—Tara S Pajoohi
(74) Attorney, Agent, or Firm—Bradley K. Lortz; Canady & Lortz LLP

(57) ABSTRACT

Methods and devices are disclosed which apply an excitation-emission matrix (EEM) to a heterogeneous, two-dimensional sample, allowing a considerably larger number of emitting, e.g. fluorescent, labels to be used simultaneously. This may be accomplished by employing a spectroscopic method of excitation-emission matrices which allows discrimination of species with similar emission spectra, and also allows positive identification of energy transfer between emitting species. The methods and devices may employ a novel excitation-light scanning technique which allows imaging of the emission from the heterogeneous sample both in two spatial dimensions (length and width) and in two spectral dimensions (excitation and emission wavelength). This light scanning technique maximizes the throughput of excitation light, increasing the sensitivity and hence the reading speed of the instrument.

23 Claims, 13 Drawing Sheets

U.S. PATENT DOCUMENTS

| | | |
|---|---|---|
| 6,704,104 B2 | 3/2004 | Li |
| 6,813,018 B2 | 11/2004 | Richman |
| 6,870,613 B1* | 3/2005 | Tisone et al. ............... 356/317 |
| 2001/0046045 A1* | 11/2001 | Dong et al. ................ 356/317 |
| 2002/0158211 A1* | 10/2002 | Gillispie ................. 250/458.1 |
| 2005/0046848 A1* | 3/2005 | Cromwell et al. .......... 356/417 |
| 2005/0123979 A1* | 6/2005 | Weiss et al. ................... 435/6 |
| 2005/0280817 A1* | 12/2005 | Horchner et al. ........... 356/318 |
| 2006/0044556 A1* | 3/2006 | Kawano .................... 356/317 |

OTHER PUBLICATIONS

Schulz et al., "Hyperspectral Imaging: A Novel Approach for Microscopic Analysis," Cytometry 43, pp. 239-247, 2001.

Martinez, et al., "Identification and removal of contaminating fluorescence from . . . ," Nucleic Acids Research, vol. 31, No. 4, e18, 2003.

* cited by examiner

MULTIPLE-LABEL FLUORESCENCE IMAGING USING EXCITATION-EMISSION MATRICES

This application claims the benefit under 35 U.S.C. §119(e) of the following U.S. provisional patent application, which is incorporated by reference herein:

U.S. Provisional Application Ser. No. 60/586,435, filed Jul. 7, 2004, by Timothy C. Corcoran, entitled "MULTIPLE-LABEL FLUORESCENCE IMAGER USING EXCITATION-EMISSION MATRICES (EEM IMAGER)-DEVICE AND METHOD".

BACKGROUND OF THE INVENTION

1. Field of the Invention

The present invention relates to systems and methods for fluorescently imaging labeled two-dimensional samples. Particularly, this invention relates to such systems and methods applied to DNA microarrays and gels used in protein and other biological or chemical separation and/or purification processes, as well as other two-dimensional fluorescent or luminescent samples.

2. Description of the Related Art

Current fluorescent imaging systems, such as those most commonly employed in biotechnology, read only a limited number of fluorescent labels simultaneously, e.g. typically two to four. In part, this fundamental limitation arises from the use of optical filters to separate the fluorescence of the different labels employed. Moreover, if a large number of different fluorescent labels were employed, performance would be very limited because all the labels would not have well separated fluorescent spectra; the spectra begin to overlap, and optical filters would no longer clearly resolve different label species under this condition.

The prior art optical filters are typically employed because they offer very good optical efficiency; losses at the desired wavelengths of light are quite small. Other spectroscopic techniques with better wavelength resolution generally have greater losses and lower throughput due to the optical devices employed (such as spectrometer slits, mirrors and gratings). This can significantly limit sensitivity and hence readout speed. Also, many prior art fluorescent imagers use lasers as fluorescence excitation sources, which the optical filter is chosen to block, minimizing scattered excitation light.

The technique of excitation emission matrix (EEM) fluorescence spectroscopy has been previously demonstrated by Warner et al. as described in Warner, I. M. et al., "Analysis of multicomponent fluorescence data," Analytical Chemistry (1977), 49(4), 564-73 and Warner, I. M. et al., "Quantitative analyses of multicomponent fluorescence data by the methods of least squares and non-negative least sum of errors", Analytical Chemistry (1977), 49(14), 2155-9. The authors showed that the composition of multicomponent mixtures can be quantitatively analyzed by the following approach. The excitation emission matrix of each known component is collected, i.e. its fluorescence intensity is measured as a function of both excitation and emission wavelengths, creating a data matrix. Similarly, the EEM of a mixture of said known components can be recorded, and its composition determined quantitatively by deconvolving the mixture EEM into its component EEMs via least squares or other programming techniques. This was successful even in cases of severe overlap and poor signal to noise ratio. However, the authors restricted their work to simple, homogenous samples and no spatial resolution was incorporated.

In addition, hyperspectral imaging allows the possibility of better spectral discrimination of fluorescent labels than the simple optical filters commonly employed in microarray labs-on-a-chip and similar sample fluorescence readers. However, hyperspectral imaging is distinct from excitation-emission matrices in that, while it separates the emission light spectrally, it does not require a multiplicity of excitation wavelengths and is typically performed with a single monochromatic excitation source. Thus, hyperspectral imaging lacks this extra spectral dimension. The imaging technique collects a data hypercube from a heterogenous sample comprising emitted light intensity as a function of position (x and y coordinates) and emission wavelength. Hyperspectral imaging has been applied to analysis of microarrays and microscopy in works such as O'Brien et al., "ASTRAL, a hyperspectral imaging DNA sequencer," Reviews of Scientific Instruments (1998), 69(5), 2141-2146; Schultz et al., "Hyperspectral Imaging: A Novel Approach For Microscopic Analysis," Cytometry (2001), 43, 239-247; and Martinez et al., "Identification and removal of contaminating fluorescence from commercial and in-house printed DNA microarrays," Nucleic Acids Research (2003), 31(4) e18.

FIG. 1A is a block diagram of a conventional spectrofluorimeter 100. The spectrofluorimeter 100 employs a lamp 102 providing a broadband (e.g., white) light 104 delivered to an excitation monochromator 106 which filters the broadband light 104 to a near-monochromatic light 108. The monochromatic light 108 from the excitation monochromator 106 is directed to the test sample 110 where the incident monochromatic light output 108 causes the test sample 110 to fluoresce. The fluorescent light 112 emitted from the test sample 110 is directed to an emission monochromator 114 which filters the fluorescent light 112 to a specific emitted monochromatic light 116. If the specific emitted monochrome light 116 is present in the fluorescent light 112, it will be detected by the detector 118 indicating the presence and amount of the target species. By scanning over a multiplicity of excitation wavelengths for each or a multiplicity of emission wavelengths, an excitation-emission matrix (EEM) may be recorded. A variety of specific prior art devices are described hereafter.

FIG. 1B is a schematic diagram of a commercial excitation-emission matrix (EEM) instrument 120. The instrument 120 operates with excitation spectral light 122 having an wavelength variation along one dimension incident on a sample 124. The excitation spectral light 122 causes fluorescent emission which is then dispersed (shown schematically as a prism 126) along a dimension perpendicular to the spectral dimension of the excitation light 122. The dispersed fluorescent emission may be captured as an image 128 representing a two-dimensional array with the excitation wavelength along one axis and the emission wavelength along the other axis. A single sampling operation of the EEM instrument 120 yields information much more rapidly than a conventional spectrofluorimeter 100 as described above in FIG. 1A, i.e., an entire excitation-emission matrix is recorded in a single reading, without the need to scan either excitation or emission wavelength.

U.S. Pat. No. 6,323,944, issued Nov. 27, 2001, and U.S. Pat. No. 6,441,892, issued Aug. 27, 2002, both by Xiao, disclose a spectrofluorimeter employing a pair of linear variable spectral filters to produce a three dimensional data output (i.e., an EEM). A collimated white light source is used that first passes through a first linear variable spectral filter, then through a sample where fluorescence occurs, then the resultant light passes through a second linear variable spectral light filter that is oriented at ninety degrees from the first filter. The light is then detected by a CCD sensor for conversion into data. This arrangement provides a very simple, rugged and compact instrument that can be used almost anywhere, such as at the scene of a contamination accident.

U.S. Pat. No. 6,597,932 by Tian et al., issued Jul. 22, 2003, discloses an instrument for evaluating fluorescence of a heterogeneous tissue including means for exciting a two-dimensional portion of the tissue surface with excitation radiation at a plurality of excitation wavelengths, means for collecting emission radiation from the two-dimensional portion of the tissue surface simultaneously with excitation of the portion, and means for forming a two-dimensional excitation-emission map of the excitation radiation and the simultaneously collected emission radiation and spatially averaging the excitation and emission radiation. Note that the approach of Tian et al. performed a homogenization of the signal from the heterogeneous sample. Accordingly, it is not an imaging technique.

U.S. Pat. No. 5,459,325 by Hueton et al., issued Oct. 17, 1995, describes a high-speed fluorescence scanner for scanning a sample at equal angles. The scanner has most of its optical components, including a light beam source, a detector, and various filters, lenses, and reflectors, in a fixed position, removed from the scan head. The lightweight scan head contains a single reflector and lens combination which is reciprocated rapidly along one axis to lengthen and shorten a region of the path of a collimated excitation beam and to form a scan line on a sample. The fluorescence emission may be gathered by the lens of the scan head and directed back, generally along the optical path of the excitation beam, to a detector. Another embodiment of the scanner places the light source, in miniature form, directly on the scan head. The sample may be translated in an axis orthogonal to the scan line in order to stimulate fluorescent emission from a two-dimensional portion of the sample. The design of the optical assembly permits scan speeds of up to approximately 100 inches per second.

U.S. Pat. No. 6,211,989 by Wulf et al., issued Apr. 3, 2001, discloses a light scanning device for exciting and detecting secondary light, especially fluorescent light, on a sample, comprising a light emission device for emitting exciting light with a wavelength suitable for exciting secondary light on or in said sample, a focusing optics for focusing the exciting light on a sub-area of said sample, a sample holding device for releasably holding the sample, a detection unit comprising a detection optics for the secondary light emitted by the sample in response to excitation and a detector device for converting the detected and imaged secondary light into electric signals. In the case of conventional known light scanning devices, scanning is carried out by means of a deflection unit consisting of tilting mirrors. Due to the long path of the light beam, positioning inaccuracies of the tilting mirrors result in major position inaccuracies of the scanning ray bundle on the surface of the sample. For avoiding this disadvantage of the prior art, the light scanning device according to the invention makes use of a sample holding device which is adapted to be rotated for rotating the sample relative to the exciting light in such a way that different sub-areas of said sample can be excited by means of the exciting light so as to emit secondary light. Due to the mechanical rotary movement of the sample, a deflection of the scanning light beam relative to the optical axis is not necessary so that precise positioning of the scanning ray bundle on the sample is possible.

Also, U.S. Pat. No. 6,172,785 by Wulf, issued Jan. 9, 2001, discloses a light scanning device for exciting and detecting secondary light, especially fluorescent light, on a sample, comprising a light-emitting device for emitting excitation light having a wavelength which is suitable for exciting secondary light on or in the sample, a scanning unit for scanning at least one sub-area of the sample with said excitation light, and a detection unit for the secondary light emitted in response to excitation of the sample, said detection unit comprising a detection optics and a detector device. In the case of conventional scanning devices, the spatial resolution on the sample is determined by the scanning element alone. If spot detectors without spatial resolution are used, the detector must be read out and re-initialized after the illumination of each scanning spot on the sample; this results in a waiting time before the scanning beam can be moved to the next scanning spot and, consequently, in a reduction of the read-out velocity. For avoiding this drawback and for increasing the read-out velocity as well as for improving the spatial resolution on the sample, the device according to the invention makes use of a detector device comprising a large number of detection elements arranged in an array with predetermined position coordinates, said detection elements being arranged in an imaging plane of the detection optics and converting light detected in spatially resolved manner into electric signals.

U.S. Pat. No. 6,704,104 by Li, issued Mar. 9, 2004, discloses an array reader having a light source configured to emit an excitation light, a substrate comprising a plurality of sites spatially configured as a two-dimensional array having a plurality of rows and a plurality of columns, where each site is configured to support a sample. The array reader includes a changing device configured to determine which of said plurality of sites is illuminated at any given instant and a detector comprising a two-dimensional array of light sensitive elements, transmission grating beam splitter (TGBS) disposed along an optical path between the substrate and the detector, and a single light focusing element disposed along an optical path between the substrate and the detector. The TGBS is configured to receive non-collimated light emitted by at least one sample illuminated by said excitation light.

U.S. Pat. No. 5,631,734 by Stern et al., issued May 9, 1997, discloses fluorescently marked targets bind to a substrate 230 synthesized with polymer sequences at known locations. The targets are detected by exposing selected regions of the substrate 230 to light from a light source 100 and detecting the photons from the light fluoresced therefrom, and repeating the steps of exposure and detection until the substrate 230 is completely examined. The resulting data can be used to determine binding affinity of the targets to specific polymer sequences.

U.S. Pat. Nos. 6,245,507 and 6,495,363, both by Bogdanov, issued Jun. 12, 2001 and Dec. 17, 2002, respectively. provide a hyperspectral imaging apparatus and methods for employing such an apparatus for multi-dye/base detection of a nucleic acid molecule coupled to a solid surface.

U.S. Pat. Nos. 6,373,568 and 6,690,466, both by Miller et al., issued Apr. 16, 2002 and Feb. 10, 2004, respectively, disclose an imaging system comprising an illuminator which produces illumination of any desired pure wavelength or of any selected mixture of pure wavelengths simultaneously, which illuminates a sample without spatio-spectral artifacts using illumination optics designed for that purpose, imaging optics, which form an image of the sample at a detector or viewing port, and a detector. This enables imaging the complete spectral image cube for a sample by taking sequential images while illuminating with a series of pure wavelengths, with greater ease and economy than by means of tunable filters, interferometers and the like. It further enables imaging while the sample is illuminated with a precisely controlled mixture of illuminant wavelengths, so that the image presented to the detector is a linear superposition of the sample properties at many wavelengths. This enables taking images of a sample that directly measure the weighted spectral properties such as projection pursuit vectors, principal components, and the like. Data acquisition is enormously simplified, and speed is increased by one to two orders of magnitude over existing techniques. This is of benefit in pathology, immunohistochemistry, Pap smear analysis, endoscopy, counterfeit detection, quality control, and other areas where one wishes to measure a spectral index of a living or inert sample.

U.S. Pat. No. 6,813,018 by Richman, issued Nov. 2, 2004, discloses a hyperspectral imager including a diffraction grating, a collecting reflecting element and a reimaging system. The diffraction grating has an entrance slit formed at an entrance slit location therein. The entrance slit has a long dimension oriented in a y-direction. The entrance slit transmits the radiation from a slice of an incoming scene image. The collecting reflecting element receives the transmitted radiation of the incoming scene image and reflects the transmitted radiation to a diffractive surface of the diffraction grating. Grooves on the diffractive surface are substantially parallel to the y-direction. The reimaging system receives radiation diffracted by the diffractive surface. The reimaging system produces a spectral image of the entrance slit at a focal surface. The spectral image provides a spectrum of radiation propagating through the entrance slit into the hyperspectral imager such that the spectrum of radiation from a first region in the y-direction can be distinguished from the spectra of radiation from other regions in the y-direction.

U.S. Pat. No. 6,427,126, by Dabiri et al., issued Jul. 30, 2002, discloses an advanced imaging spectrograph system and method are provided for very high throughput identification, sequencing and/or genotyping of DNA and other molecules. The system is based on the integration of improved electrophoresis structures with an imaging spectrophotometer that records the entire emission spectra along an imaging line across a sequencing gel (or capillary array). The system includes spectral shape matching to improve dye identification allowing the use of dyes having nearly any emission spectra and allowing greater than four dye multiplexing.

U.S. Pat. No. 6,495,818, by Mao, issued Dec. 17, 2002, discloses a microscopic hyperspectral imaging scanner that has a microscopic front objective lens, a spatial window for selectively passing a portion of the image therethrough, and a CCD array for receiving the passed portion of the image. The spatial window and CCD array are mounted for tandem reciprocating movement relative to the front object lens. In one embodiment, the spatial window is a slit and the CCD array is one-dimensional, and successive rows of the image in the focal plane of the front objective lens are passed to the CCD array by an image relay lens interposed between the slit and the CCD array. In another embodiment, the spatial window is a slit, the CCD array is two-dimensional, and a prism-grating-prism optical spectrometer is interposed between the slit and the CCD array so as to cause the scanned row to be split into a plurality of spectral separations onto the CCD array. In another embodiment, the CCD array is two-dimensional and the spatial window is a rectangular linear variable filter ("LVF") window, so as to cause the scanned rows impinging on the LVF to be bandpass filtered into spectral components onto the CCD array through an image relay lens interposed between the LVF and the CCD array.

U.S. Pat. No. 6,490,075, by Scheps et al., issued Dec. 3, 2002, discloses an acousto-optic tunable filter hyperspectral imaging system which has applications that include detecting color variation in a region, for example, color variations due to temperature changes in an area of ocean water, and, in a more specific application, detecting bioluminescence of certain organisms known to attach themselves to various objects. In one aspect of the invention, an acousto-optic tunable filter hyperspectral imaging system is moved across the region to collect a series of images in which each image represents the intensity of light at a different wavelength. In one embodiment, the acousto-optic tunable filter hyperspectral imaging system includes a motion platform for positioning the acousto-optic tunable filter hyperspectral imaging system over successive Y-coordinates of a region in a direction substantially parallel to a direction of motion of the motion platform. In one such embodiment, the motion platform may be an aircraft or any other platform suitable for moving the acousto-optic tunable filter hyperspectral imaging system over the region.

U.S. Pat. No. 6,337,472, by Garner et al., issued Jan. 8, 2002, discloses a filter-less imaging microscope and method for analyzing samples on a slide at multiple wavelengths of light comprising, a microscope, a light dispersive element positioned to receive images from the microscope at multiple wavelengths, the light dispersive element producing an array of light from the image and a camera positioned to detect the light array produced by the light dispersive element, wherein the camera detects the light array dispersed by the light dispersive element at multiple wavelengths, is disclosed. The camera can detect the entire spectrum of light produced by the light dispersive element.

U.S. Pat. No. 5,379,065, by Cutts, issued Jan. 3, 1995, discloses a hyperspectral imager including a focal plane having an array of spaced image recording pixels receiving light from a scene moving relative to the focal plane in a longitudinal direction, the recording pixels being transportable at a controllable rate in the focal plane in the longitudinal direction, an electronic shutter for adjusting an exposure time of the focal plane, whereby recording pixels in an active area of the focal plane are removed therefrom and stored upon expiration of the exposure time, an electronic spectral filter for selecting a spectral band of light received by the focal plane from the scene during each exposure time and an electronic controller connected to the focal plane, to the electronic shutter and to the electronic spectral filter for controlling (a) the controllable rate at which the recording is transported in the longitudinal direction, (b) the exposure time and (c) the spectral band so as to record a selected portion of the scene through M spectral bands with a respective exposure time $t_q$ for each respective spectral band q.

In view of the foregoing, the prior art does not demonstrate a method for combining the advantages of the EEM in quantitative analysis of fluorescent species which have substantially overlapped spectra, with imaging capability necessary for spatially characterizing a sample consisting of a two-dimensional, heterogeneous array. There is also a need in the art for fluorescent imaging systems and methods that increase data throughput by the ability to handle a larger number of fluorescent species simultaneously while providing good quantitative accuracy and exhibiting reduced sample-to-sample variation. In addition, there is a need for such systems and methods to be cost effective. As detailed hereafter, these and other needs are satisfied by the present invention.

SUMMARY OF THE INVENTION

Various embodiments of the invention address the process of imaging fluorescently labeled heterogeneous, two-dimensional samples, such as microarrays, labs-on-a-chip and gels used in genetic, protein and other separation and/or purification processes, as well as other two-dimensional fluorescent samples. Embodiments of the invention allow a considerably larger number of fluorescent labels to be used simultaneously than previously. This may be accomplished by employing a spectroscopic technique using an EEM which allows discrimination of species having similar fluorescent spectra. In addition, embodiments of the invention may employ a novel excitation-light scanning technique to maximize the throughput of excitation light, increasing the sensitivity and reading speed.

A typical embodiment of the invention comprises a light source for producing spectral excitation light having wavelength variation along a first dimension across a spectral range, a scanning device for scanning the spectral excitation light across a sample substantially parallel to the first dimension where the spectral excitation light interacts with the sample to emit a fluorescent, luminescent, or other secondary emission light and an imaging spectrograph with a two-dimensional detector for capturing the sample emission light having wavelength variation along a second dimension. The sample may comprise a width and the spectral excitation light comprises a repetition of the spectral range along the first dimension such that a single scan of the spectral excitation light across the sample exhibits the spectral range to each point across the width in a stepwise fashion. Typically, the sample may comprise a two-dimensional array, including but not limited to such items as a DNA microarray, a protein microchip, an electrophoresis gel, a slice of tissue, or some other material with fluorescent or luminescent properties.

In further embodiments, the apparatus may include a movable platform supporting the sample for moving the sample along a direction distinct from the first dimension (e.g., perpendicularly) following completion of each scan of the spectral excitation light across the sample. The light source may comprise a lamp and a wavelength dispersion device, such as a spectrometer. The imaging device may comprise another wavelength dispersion device, e.g. an imaging spectrograph, with a two-dimensional detector such as a charge-coupled device (CCD). With each step in spectrally scanning the excitation light, the image of the sample emission (spatially distinct in one dimension and spectrally dispersed in the other direction) may be recorded with a frame grabber or similar device and stored as a data hypercube (comprising the and excitation-emission matrix) on a computer.

Scanning of the spectral excitation light may be accomplished in different ways. For example, the scanning device may comprise a tiltable scanning mirror for reflecting the spectral excitation light and moving the reflected spectral excitation light across the sample substantially parallel to the first dimension. Alternately, the scanning device may comprise a movable platform supporting the sample for moving the sample substantially parallel to the first dimension. Alternatively, the scanning mirror and relay lens may be mounted on a moving platform such that they can be linearly translated with respect to the sample substantially parallel to the first dimension. Any of these scanning modalities may be implemented in a stepwise fashion.

In further embodiment the stored excitation-emission matrix may be analyzed with a data processor. Operating on the data of the excitation-emission matrix, the data processor can identify sample emission due to energy transfer between at least two emitting species. In addition, the data processor can also identify a signature in the data of the excitation-emission matrix of a donor species and an acceptor species having the properties of the donor species along an excitation wavelength axis and the properties of the acceptor species along an emission wavelength axis. Furthermore, the data processor can correct error in quantification of amount of the at least two emitting species due to the energy transfer between the at least two emitting species from the data of the excitation-emission matrix.

In one exemplary apparatus embodiment of the invention, the device comprises a broadband light source, such as a tungsten filament lamp, collection and focusing optics for the light source, an excitation spectrometer, a scanning mirror, a sample platform capable of translation, and relay optics to collect the sample emission subsequent to excitation and refocus the light on the entrance slit of an emission imaging spectrograph, oriented substantially parallel to the direction along which the excitation light is scanned across the sample. The emission imaging spectrograph is equipped with a two-dimensional array detector. The scanning mirror may be manipulated with a motor and controller device. Likewise, the sample stage may also manipulated with a motor and controller. Additional relay and focusing optics may be used with the scanning mirror. Both motors may be controlled by the data processor. The array detector may comprise a charge-coupled detector or similar device.

Similarly, a typical method of the invention includes the operation of producing spectral excitation light having wavelength variation along a first dimension across a spectral range, an operation of dispersing the spectral excitation light across a line on the sample substantially parallel to the first dimension where the spectral excitation light interacts with the sample to emit a fluorescent light, and an operation of capturing the fluorescent light as a spectral emission light having wavelength dispersion along a second dimension distinct from the direction of dispersion of the excitation light. Producing the spectral excitation light may be performed by repeating the spectral range along the first dimension such that scanning the spectral excitation light in a stepwise fashion across the sample sequentially exhibits the spectral range to each point across the width of the sample, at each step collecting the spectral emission light dispersed in the manner described above. In this fashion, the excitation emission matrix for a series of closely spaced points in space along the illuminated line of the sample may be constructed, using a computer or other data processor to index the data hypercube collected from the array detector at each step. Furthermore, the sample may be moved substantially perpendicular to the first dimension following each scan of the spectral excitation light across the sample, exposing a new line of the sample substantially adjacent to and parallel with the previous one. In this fashion, excitation emission matrices may be constructed for an array of points across the surface of the sample.

Producing the spectral excitation light can be performed by producing and diffracting a broadband light and capturing the fluorescent light can be performed by diffracting the fluorescent light along the second dimension. The scanning operation may be accomplished by reflecting the spectral excitation light and moving the reflected spectral excitation light across the sample substantially parallel to the first dimension. Alternately, scanning may be performed by moving the sample substantially parallel to the first dimension.

BRIEF DESCRIPTION OF THE DRAWINGS

Referring now to the drawings in which like reference numbers represent corresponding parts throughout.

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

1. Overview

The present invention discloses methods and devices which apply an excitation-emission matrix (EEM) to a heterogeneous, two-dimensional sample, allowing a considerably larger number of fluorescent labels to be used simultaneously. This may be accomplished by employing a spectroscopic method of excitation-emission matrices which allows discrimination of species with similar fluorescent spectra. Embodiments of the invention may employ a novel excitation-light scanning technique which maximizes the throughput of excitation light, increasing the sensitivity and hence the reading speed of the instrument. None of the instruments or methods described in the prior art above are capable of using an EEM for imaging as with the present invention.

Excitation-emission matrices (EEMs) are matrices of fluorescence (emission) spectra data collected from a sample over a range of excitation wavelengths. The data may be represented in topographical map format, with the excitation wavelength forming the y-axis (north-south), the emission wavelength forming the x-axis (east-west) and the fluorescence intensity forming the z-axis (height). The emission data from every fluorescing species appears as a feature, e.g. a "mountain" on such a map in a characteristic location. Species which exhibit overlapping fluorescence spectra may still be resolved if their wavelength of maximum excitation sensitivity is somewhat distinct. For example, they may appear as adjacent peaks in a mountain range. Extraneous light scatter appears as a diagonal ridge which occurs at a clearly defined location on the map, displaced from the topographic features indicating the fluorescing species. If one knows the placement of the characteristic feature of each fluorescent label, then an EEM recorded from a mixture of labels (e.g. appearing as a "mountain range") can be readily decomposed into its component features, and the type and amount of each fluorescent species can be determined therefrom.

In order to excite a large number of labels, the excitation-emission matrix method requires a multiplicity of excitation wavelengths, various embodiments of the invention employ a broadband light source, such as a lamp, instead of a laser to excite fluorescence. When using such a broadband light source, care must be taken that light scatter does not pose problems. The EEM ameliorates these problems by placing such light scatter in a distinct, predictable location within the data set which is separated from the data of interest.

2. Fluorescence Spectroscopy

Figure 1A:
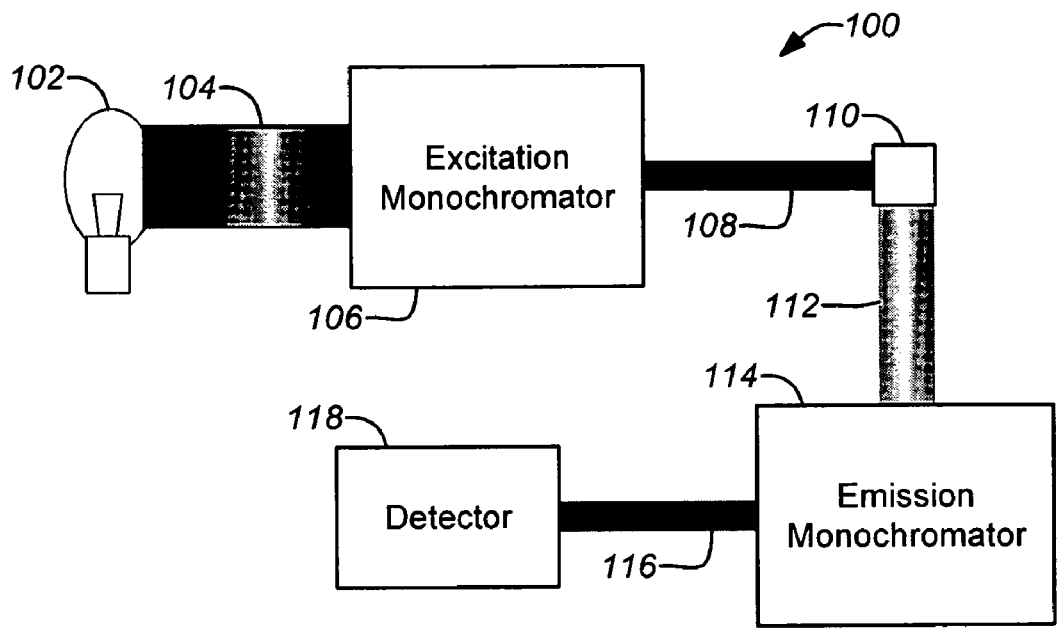
FIG. 1A is a block diagram of a conventional spectrofluorimeter.
Figure 1B:
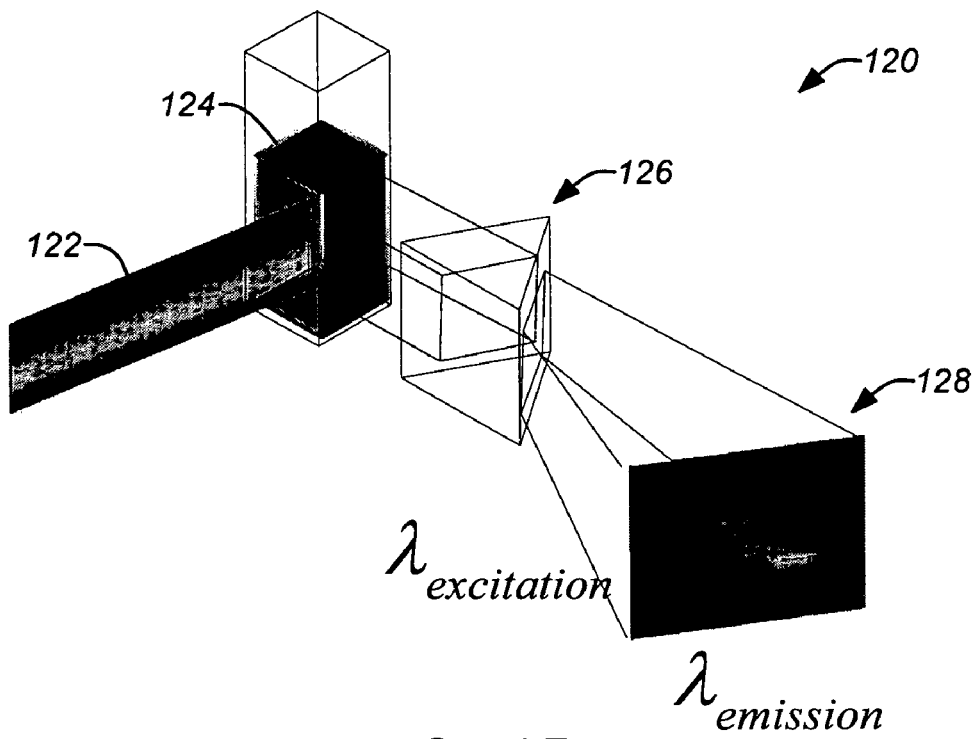
FIG. 1B is a block diagram of a commercial excitation-emission matrix (EEM) instrument.

Fluorescence spectroscopy operates through the mechanism that particular species (i.e. composition prepared with an appropriate label dye) will fluoresce emitting a signature light wavelength when excited with a particular light wavelength. The species and amount can be determined from the emitted light. See e.g., the conventional spectrofluorimeter of FIG. 1A previously discussed.

Figure 2A:
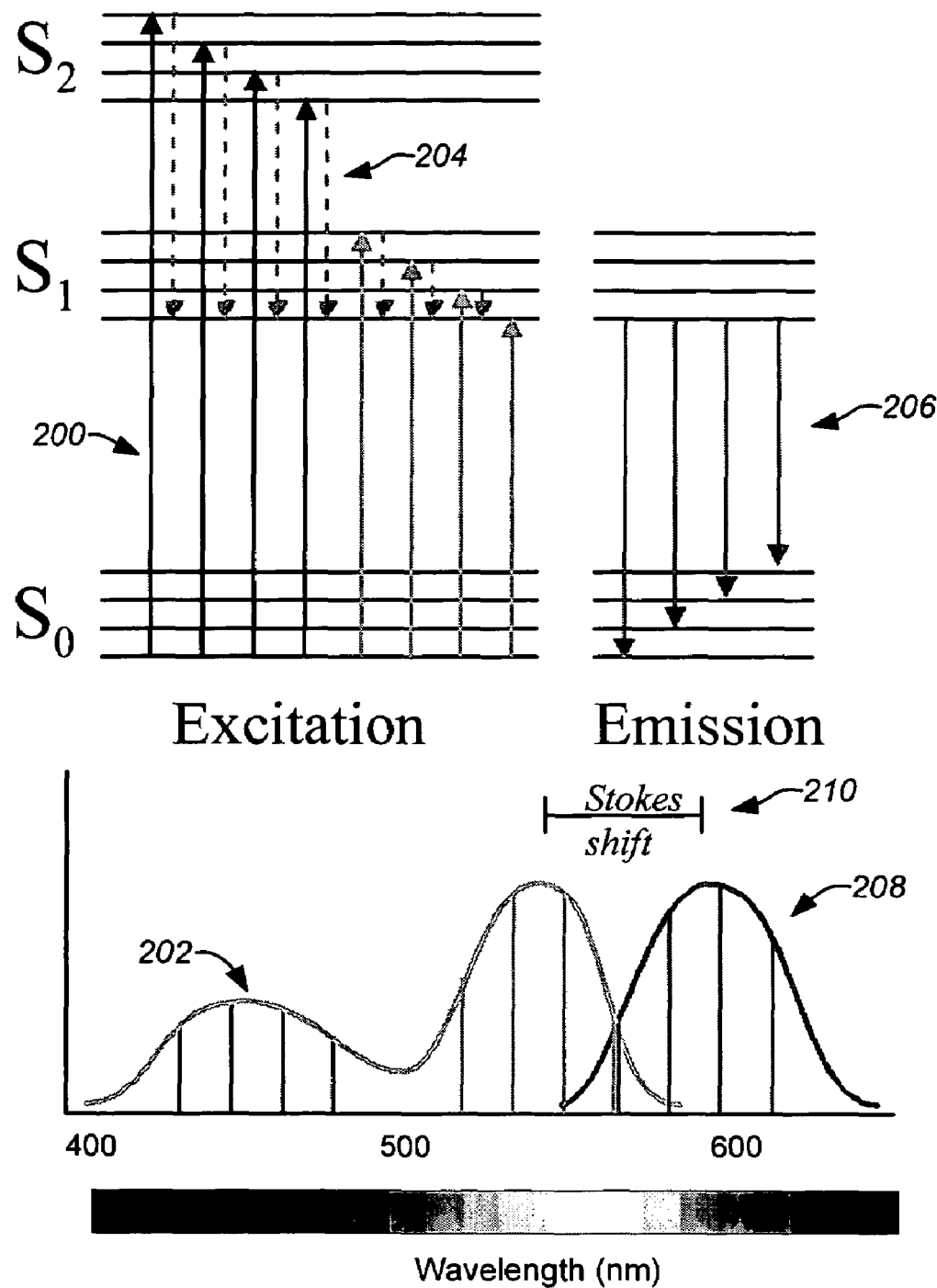
FIG. 2A illustrates the relationship of excitation and emission spectra.

FIG. 2A illustrates the relationship of excitation and emission spectra in fluorescence spectroscopy. Molecular fluorescence begins with the absorption of light energy (photons) by a molecule. The molecule is excited, absorbing this additional energy by shifting an electron to a higher energy state. In FIG. 2A this is illustrated with the first series of upward arrows from the ground energy state $S_0$ to the upper energy states $S_1$ and $S_2$ 200. The corresponding excitation light is shown in the lower graph by the first profile 202. A portion of the excitation energy can be released several different ways. For example, the molecule may lose some of the energy through vibrations as indicated by the series of downward arrows from various energy levels in states $S_2$ and $S_1$ to the lowest energy level in $S_1$ 204. Fluorescence occurs when the molecule releases that remainder of the excitation energy by emitting light as shown by the downward arrows from $S_1$ to $S_0$ 206. The corresponding emission light is shown in the lower graph by the second profile 208. Because of the energy loss due to molecular vibration in between the absorbance and emission processes, the fluorescence is typically lower energy having a larger wavelength than the absorbance. This is difference is known as the Stokes shift 210.

Figure 2B:
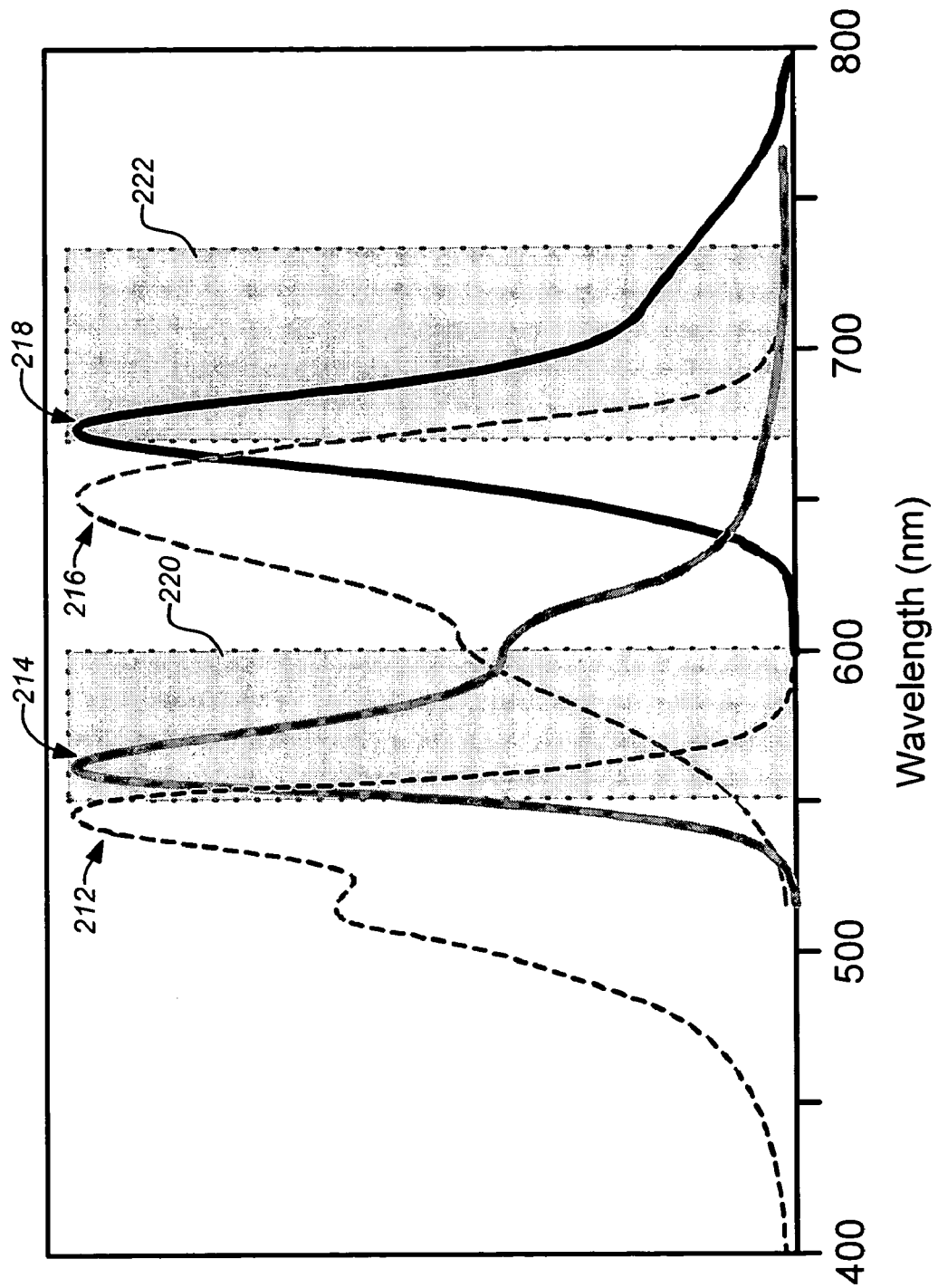
FIG. 2B illustrates excitation and emission of typical label dyes.

FIG. 2B illustrates excitation and emission of some typical label dyes in fluorescence spectroscopy. The first excitation wavelength profile 212 yields an emission wavelength profile 214 corresponding to a Cy3 dye. Similarly, the second excitation wavelength profile 216 yields an emission wavelength profile 218 corresponding to a Cy5 dye. The first and second grey regions 220, 222 represent filters applied to the detector to appropriately isolate the respective emission wavelengths for Cy3 and Cy5.

3. Excitation-Emission Matrices

Figure 3A:
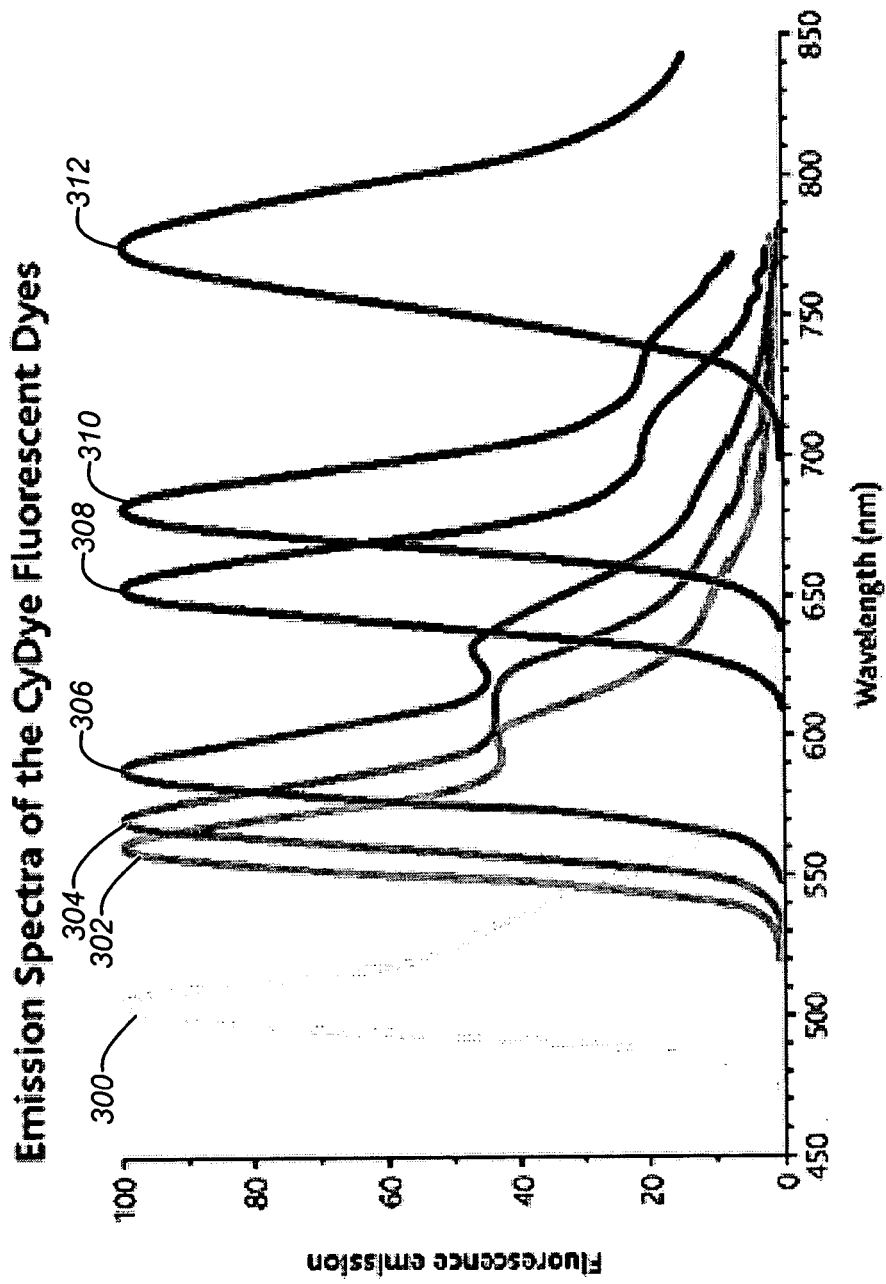
FIG. 3A shows a graph illustrating the problem of overlap using multiple label dyes.

FIG. 3A shows a graph illustrating the problem of overlap using multiple label dyes. The graph shows the emission spectra of a variety of CyDye fluorescent dyes, Cy2 300, Cy3 302, Cy3B 304, Cy3.5 306, Cy5 308, Cy5.5 310 and Cy7 312, employed in fluorescence spectroscopy. The close proximity and overlap of many of the emission spectra prevents distinguishing the separate dyes if employed in combination with the commonly used method of optical filters.

Figure 3B:
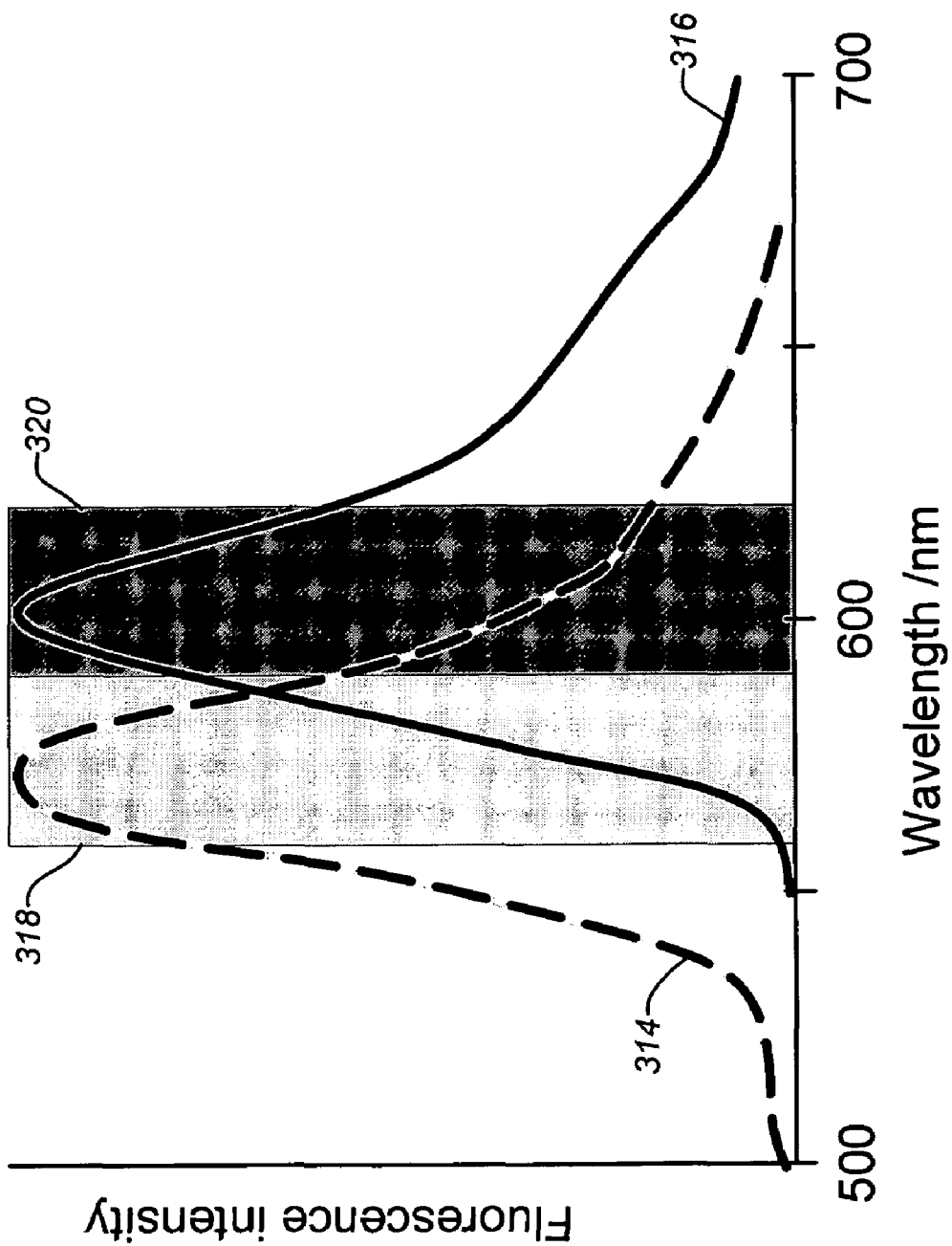
FIG. 3B shows a graph illustrating the problem of overlap using two adjacent label dyes.

FIG. 3B shows a graph illustrating the problem of overlap using two adjacent label dyes. Here, the two adjacent emission spectra 314, 316 of different dyes can result in false positives for one of the other dye as shown by the significant portions of overlapping spectra 314, 316 into the respective filters 318, 320 of the other dye. To improve on this, the use of an excitation-emission matrix (EEM) can resolve data in three distinct dimensions, excitation and emission wavelength and fluorescence intensity.

Figure 4A:
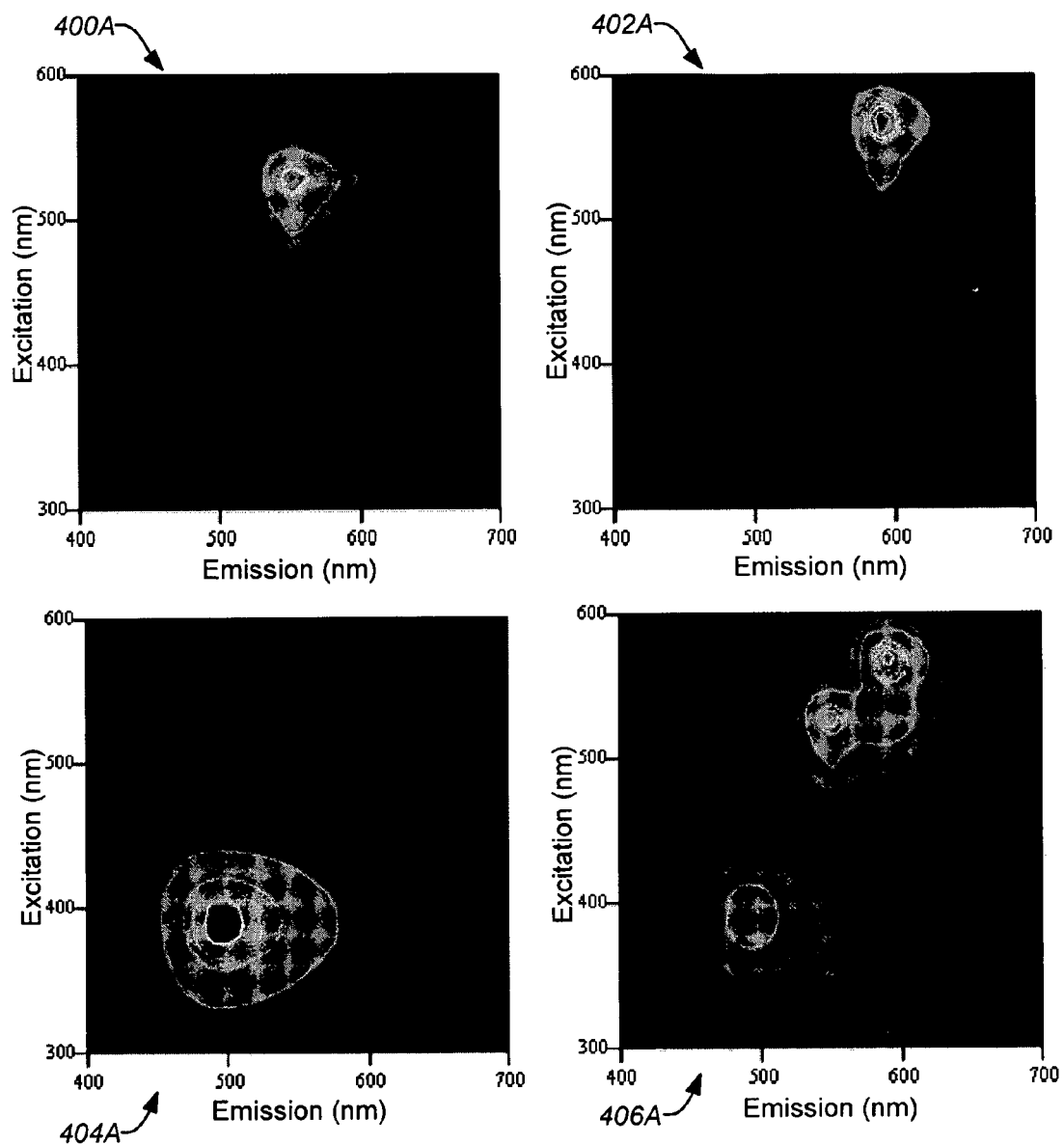
FIGS. 4A and 4B illustrate EEM images and graphs of three dyes alone and in combination.
Figure 4B:
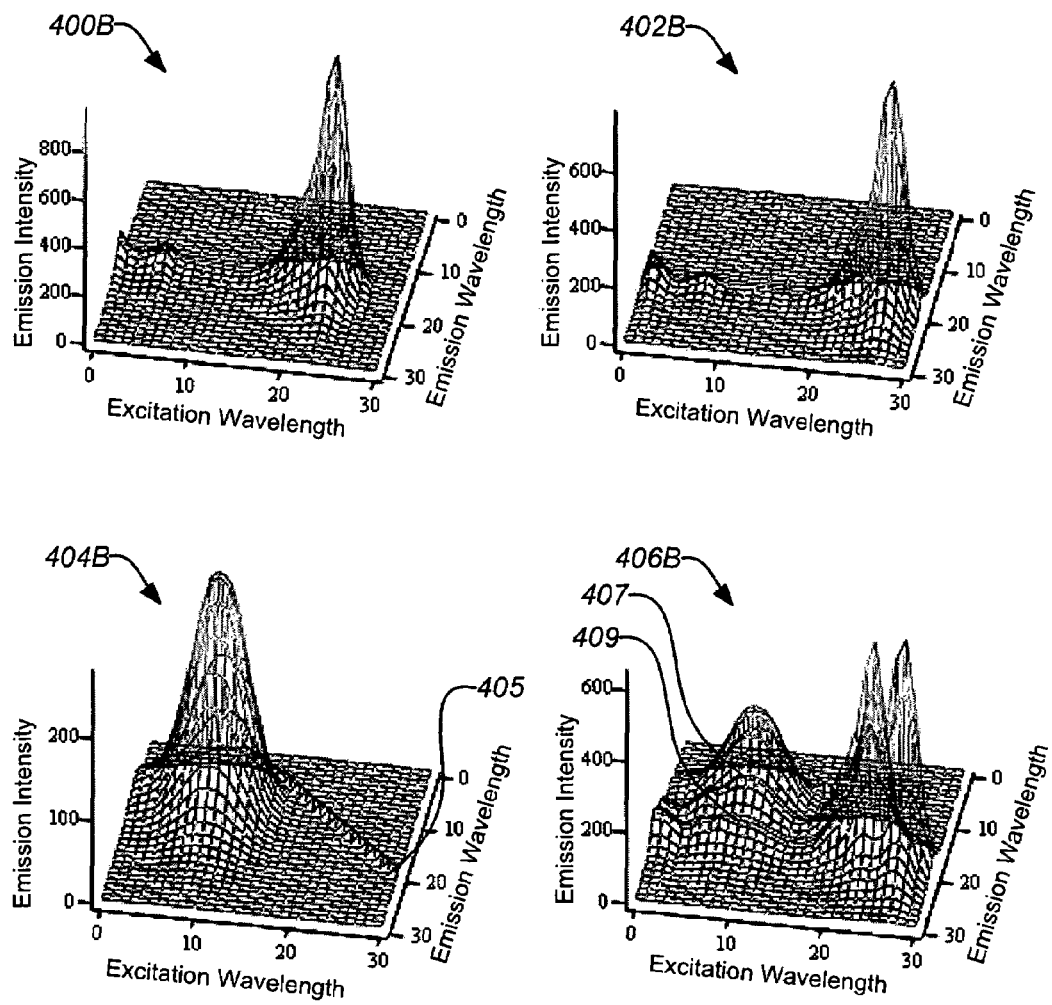

FIGS. 4A and 4B illustrate EEM images and graphs of three dyes alone and in combination. The grayscale contour maps 400A, 402A, 404A of FIG. 4A respectively show EEMs of three dyes, Rhodamine-590, Rhodamine-610 and Coumarin-500. Similarly, the same EEMs of the same three dyes are shown in the topographical maps 400B, 402B, 404B of FIG. 4B. Similarly, the contour map 406A of FIG. 4A and the topographical map 406B of FIG. 4B show an EEM of a combined mixture of the same three dyes. Evident in the combination maps 406A, 406B are the distinct peaks from the individual dye EEMs. The characteristic appearance of scattered light is visible as a ridge in the data, 405. In addition, cross-talk peaks 407 and 409 are also exhibited at common excitation/emission intersection points between the dye peaks, e.g. the excitation wavelength of Coumarin-500 and the emission wavelengths of Rhodamine-590 at peak 407 and Rhodamine-610 at peak 409. These cross-talk peaks are due to energy transfer from one dye species to another, which commonly occurs when dyes with similar spectral characteristics are in close proximity to one another.

Figure 4C:
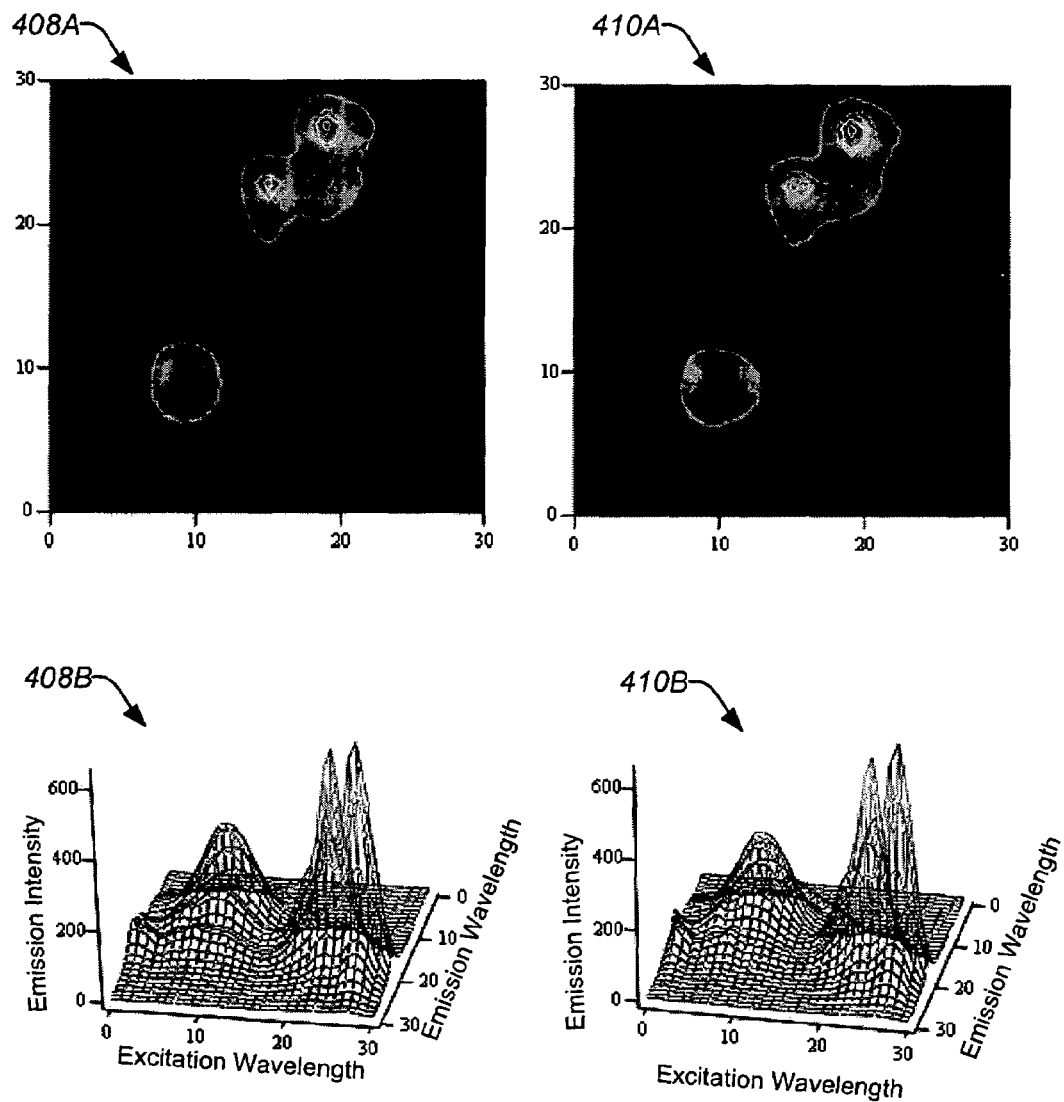
FIG. 4C compares least squares fitting of individual EEMs to an EEM of a dye combination.

FIG. 4C compares least squares fitting of individual EEMs to an EEM of a dye combination. The contour map 408A and topographical map 408B are the result of a dye mixture. An EEM of the mixture can be generated from a combination of the individual dye EEMs as shown in the contour map 410A and topographical map 410B. It is also clear that a combination of the individual species' EEMs does not produce the energy transfer peaks; these distinct signatures only occur when donor and acceptors are present together. Accordingly, a mixture's composition may be determined from individual dye EEMs. The by extending the application of EEMs to include imaging capability, they may be applied to a two dimensional array sample to yield five dimensional data.

Figure 5:
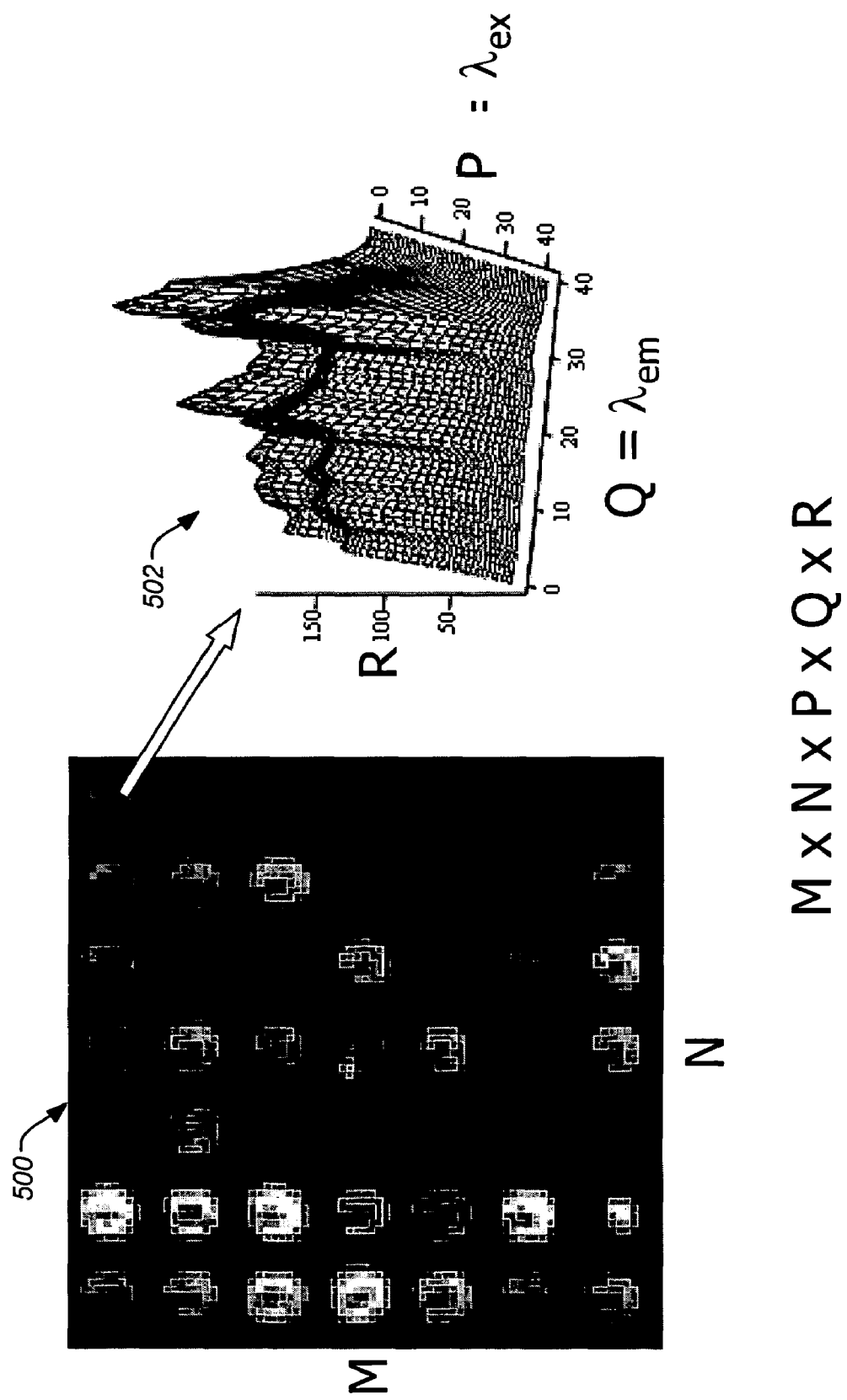
FIG. 5 illustrates five dimensional data available in a gene microarray.

FIG. 5 illustrates five dimensional data available in gene microarray. The two spatial dimensions of the sample may be called M and N. The two spectral dimensions of the EEM may be called P (excitation wavelength, $\lambda_{ex}$) and Q (emission wavelength, $\lambda_{em}$). EEM imaging records an emission intensity, R, across P×Q for each spatial position (M×N). An EEM can be developed for each spatial position in the M×N microarray 500. For example, the sample in the first row and Nth column yields the EEM 502 comprising an excitation wavelength dimension, P, an emission wavelength dimension, Q, and a fluorescence intensity dimension, R. Accordingly, the five dimensional data, called a data hypercube, include M, N, P, Q and R. Hyperspectral imaging is distinct from EEM imaging. Phrased in the language used above, it records the dimensions M, N, Q and R, but does not attempt to systematically include a range of P values in the data hypercube.

While EEMs have been known since 1977, their use has been restricted to samples which are either homogenous or in which their heterogeneities are averaged out by the sampling process (e.g. as in U.S. Pat. No. 6,597,932 described above). EEMs can employ two spectrometers, one for selecting a single excitation wavelength, the other for selecting a single emission wavelength. However, optical efficiency is often poor in such systems. The technique shown in U.S. Pat. Nos. 6,441,892 and 6,323,944, described above, obviates some of the optical efficiency problems. However, this technique is not amenable to imaging because it records a single EEM sampling over a significantly extended region of sample positions. Thus, the process averages out spatial heterogeneities.

4. Excitation-Emission Matrix Imager

Embodiments of the present invention enable the ability to perform EEMs with spatial resolution providing an imaging capability. As only two dimensions plus emission intensity can be imaged on an array detector at one time, five dimensions of data may be collected by imaging in conjunction with two scanning operations. Embodiments of the invention may record emission intensity R of the imaged M×Q data on an array detector. The excitation wavelength P, which is spectrally dispersed across the sample substantially parallel to the M dimension, is then displaced somewhat along this same dimension and the M×Q×R data on the detector is recorded again. As P is not constant across the range of M, the value of P at each given moment for each value M must be recorded in the data set. This is repeated in a stepwise fashion until each spatial position along M has been exposed to the full range of P values desired. This scan is termed a P-scan. At this point, a data hypercube of dimensions M×P×Q×R has been collected. The sample is then stepped in a second dimension (e.g the N dimension, termed an N-scan) and the P-scan process is repeated. In this fashion, the full data hypercube M×N×P×Q×R is collected. The details and advantages of this approach are described below.

Figure 6A:
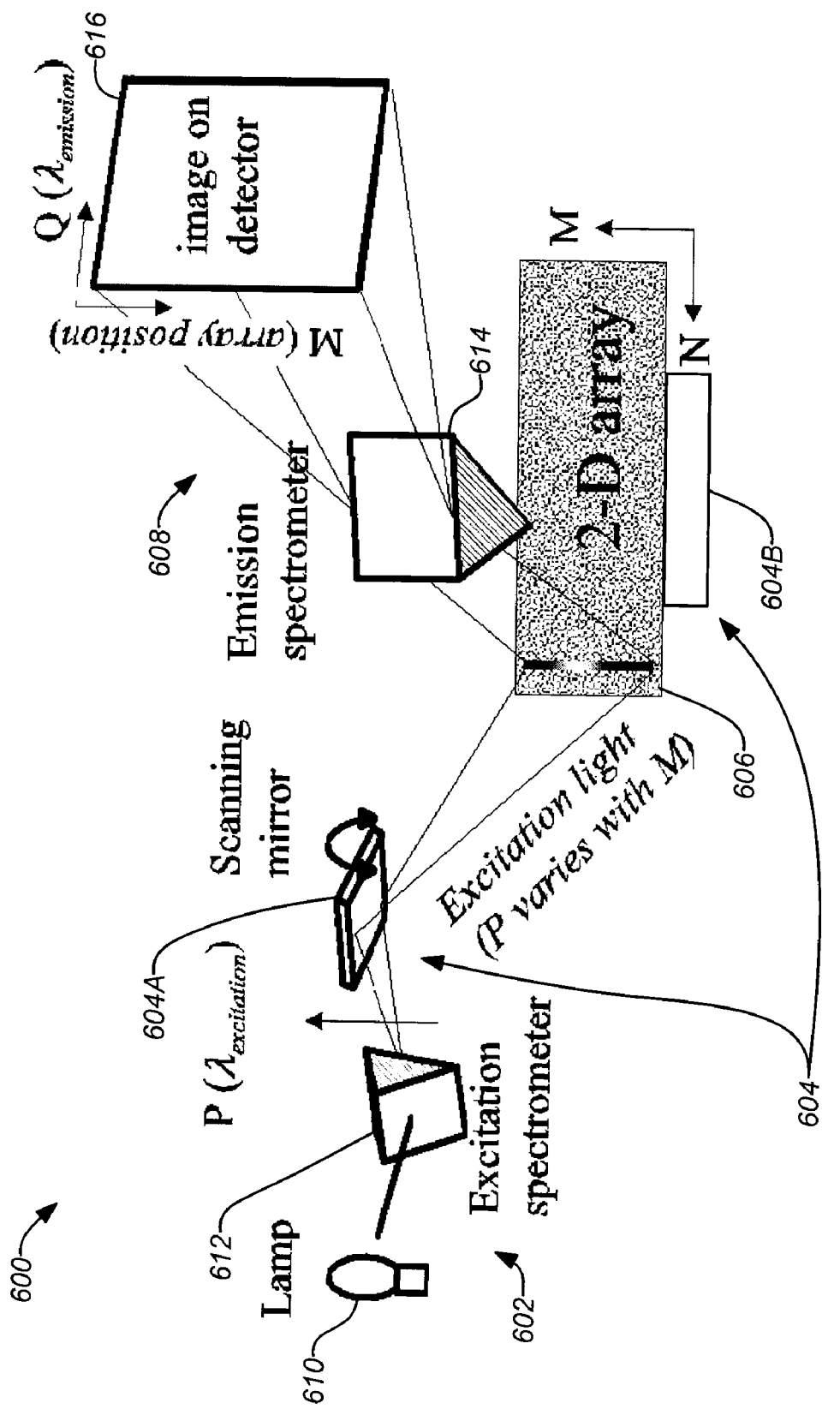
FIG. 6A is schematic diagram of a multiple-label fluorescence imager embodiment of the invention using excitation-emission matrices.

FIG. 6A is a schematic diagram of the multiple-label fluorescence imager using excitation-emission matrices which may be described as an EEM imager. Focusing optics have been omitted and spectrometers depicted as simple prisms for clarity. Also not shown are control electronics for the detector and for the motors which may scan the mirror (P scan) and/or the stage or platform upon which the sample rests (N scan). Further, a computer may be used to control operation of the device along with collecting and correlating the data.

The apparatus 600 comprises a light source 602 for producing spectral excitation light having wavelength variation along a first dimension (P) across a spectral range. The apparatus 600 also includes a scanning mirror 604A and movable platform 604B (the scanning mirror 604A and/or movable platform 604B may be referenced as scanning device 604) for scanning the spectral excitation light across a sample 606 substantially parallel to the first dimension (P along M) where the spectral excitation light interacts with the sample 606 to emit a secondary, e.g., fluorescent, light. The apparatus 600 also includes an imaging device 608 for capturing the emitted light having wavelength variation along a second dimension (Q). Typically, the sample 606 may comprise a two-dimensional array, such as a microarray, lab-on-a-chip, or an electrophoresis gel.

In further embodiments, the apparatus 600 may include a movable platform 604B supporting the sample 606 for moving the sample 606 along a second dimension (e.g. along N) distinct from the first dimension (M) following each scan of the spectral excitation light across the sample 606. In addition, the light source 602 may comprise a lamp 610 and a wavelength dispersion device 612, such as a prism or grating. The imaging device 608 may comprise a second wavelength dispersion device 614, e.g. another prism or grating, and a two-dimensional detector 616, e.g. a charge-coupled device (CCD).

Scanning of the spectral excitation light may be accomplished in different ways. For example, the scanning device 604 may comprise a scanning mirror 604A for reflecting the spectral excitation light and moving the reflected spectral excitation light across the sample 606 substantially parallel to the first dimension (P along M). This may be done by tilting the mirror or by translating the mirror and relay lens along the aforementioned dimension. Alternately, the scanning device 604 may comprise a movable platform 604B supporting the sample 606 for moving the sample 606 substantially parallel to the first dimension (P along M). In addition, the scanning device 604 may comprise a combination of both a scanning mirror 604A and a movable platform 604B operated together to yield scanning of the spectral excitation light across the sample 606.

Operation of the device 600 may be described as follows. In the first dimension scan (the P scan), the light from the excitation lamp 610 may be dispersed spectrally (i.e. multiple P values spread out in space) into a narrow stripe across the sample along the M axis. The sample emission is collected from this stripe and imaged onto the input slit of the emission spectrometer, which spectrally disperses the emission along the Q dimension in a direction substantially perpendicular to the entrance slit, and images the emission onto an array detector 616 (such as a charge-coupled device, or CCD).

The image on the detector 616 then is a matrix with dimensions M×Q×R. At a given moment in the P-scan, each M value also corresponds to a distinct value of P. In order to collect the EEM it is necessary to scan the value of P for each position M on the sample. This may be performed by deflecting the excitation light stripe spatially across the sample 606 along the M axis by moving a mirror while repeatedly recording M×Q images. In this fashion, at each spatial point M, for every selected value of P (excitation), an emission spectrum is collected (Q×R). From this data, an EEM (P×Q×R) is assembled for each value of M. Thus, imaging along a linear stripe (in the M direction) of the sample 606 is produced. To obtain imaging over the entire two-dimensional array sample 606, the sample 606 is simply translated in the N direction by a movable platform 604B or mechanical stage (representing the N scan) and another EEM. This process of obtaining EEMs for each value of M at the new position N is repeated across the entire sample 606.

Embodiments of the invention improve the overall data acquisition rate over prior art devices. In part, data throughput is enhanced by maximizing sensitivity of the apparatus by maximizing the light throughput. Although the process described above would be simpler to describe if only one value of excitation wavelength P were used at a time, it would abandon most of the available power of the lamp. By utilizing a wide spectral range of the lamp output, a much larger portion of its power can be used effectively. In addition, embodiments of the invention may further improve light throughput by using low f number, high efficiency spectrographs (e.g. employing either diffraction gratings or prisms).

Figure 6B:
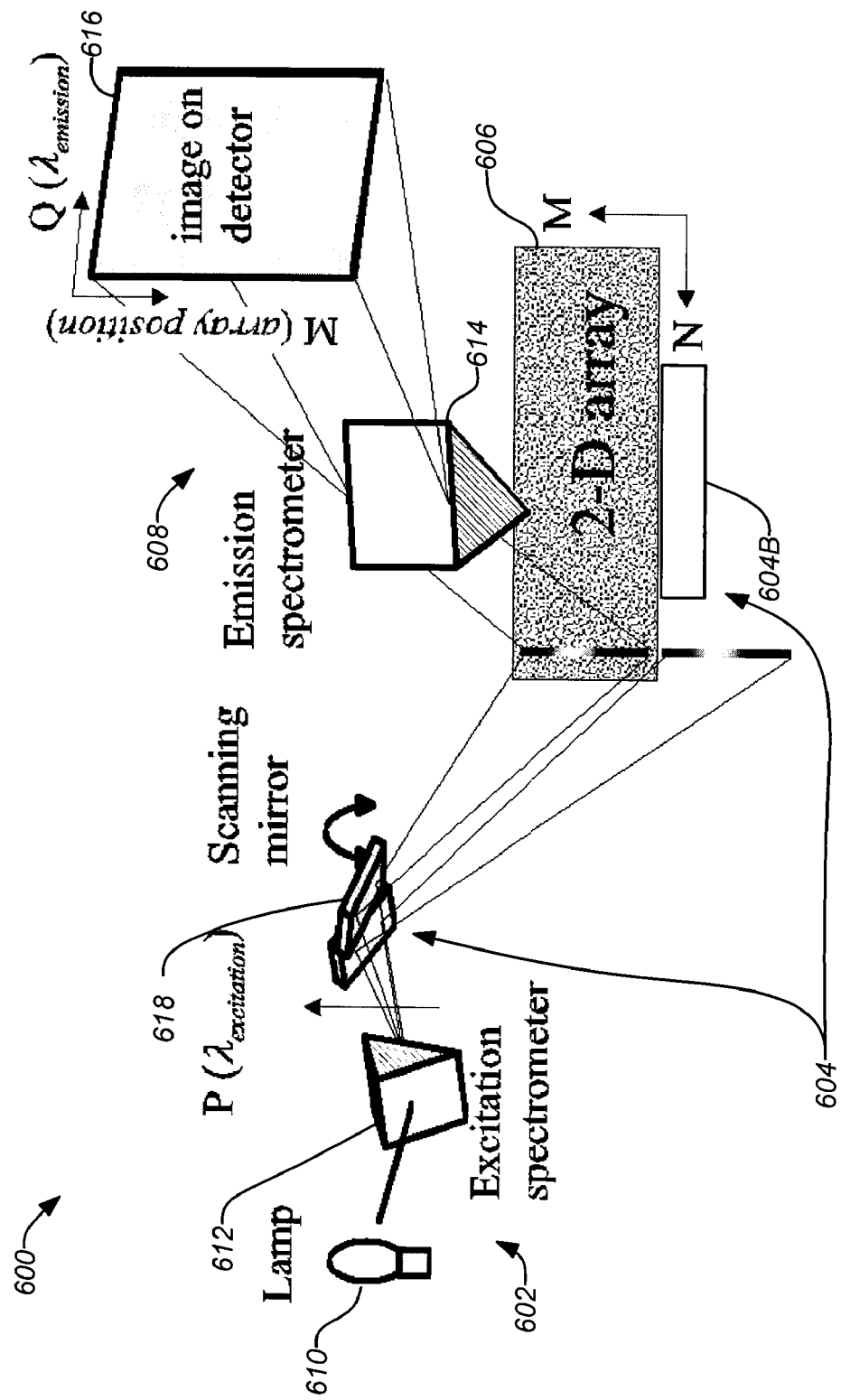
FIG. 6B is a schematic diagram of an alternate excitation-emission matrix imager embodiment of the invention using two excitation stripes on the sample to increase data throughput.

FIG. 6B illustrates an alternate embodiment of the EEM imager 600, using two excitation stripes on the sample to increase data throughput. Employing a split scanning mirror 618 (which may also operate as a scanning device 604 described above) is one way to implement this. The split scanning mirror 618 reflects the excitation light into two or more adjacent stripes disposed end to end. The spectral excitation light comprises a repetition of the spectral range along the first dimension such that a single scan of the spectral excitation light across the sample exhibits the spectral range to each point across the width. Thus, instead of a single stripe of excitation light across the sample as shown above, repeated stripes of excitation light may be employed, each with the same value N. For example, both stripes may lie along the same line, one behind the other. The repeated second stripe may be created by splitting the scanning mirror into two parts, slightly angled from each other with respect to the tilt axis of the mirror. This implementation allows excitation light to be continuously presented to each spot M of the sample 606, increasing light throughput as P is scanned by the scanning device 604 (mirror 618 and/or movable platform 604B). It is important to note that the use of a repetition of the spectral range in this manner is not limited to using a particular spectral range in the stripes. Various spectral ranges may be used in two or more stripes which may be the same or different as long (depending upon the application) as a continuous scan yields continuous fluorescence data from a sample width.

Figure 6C:
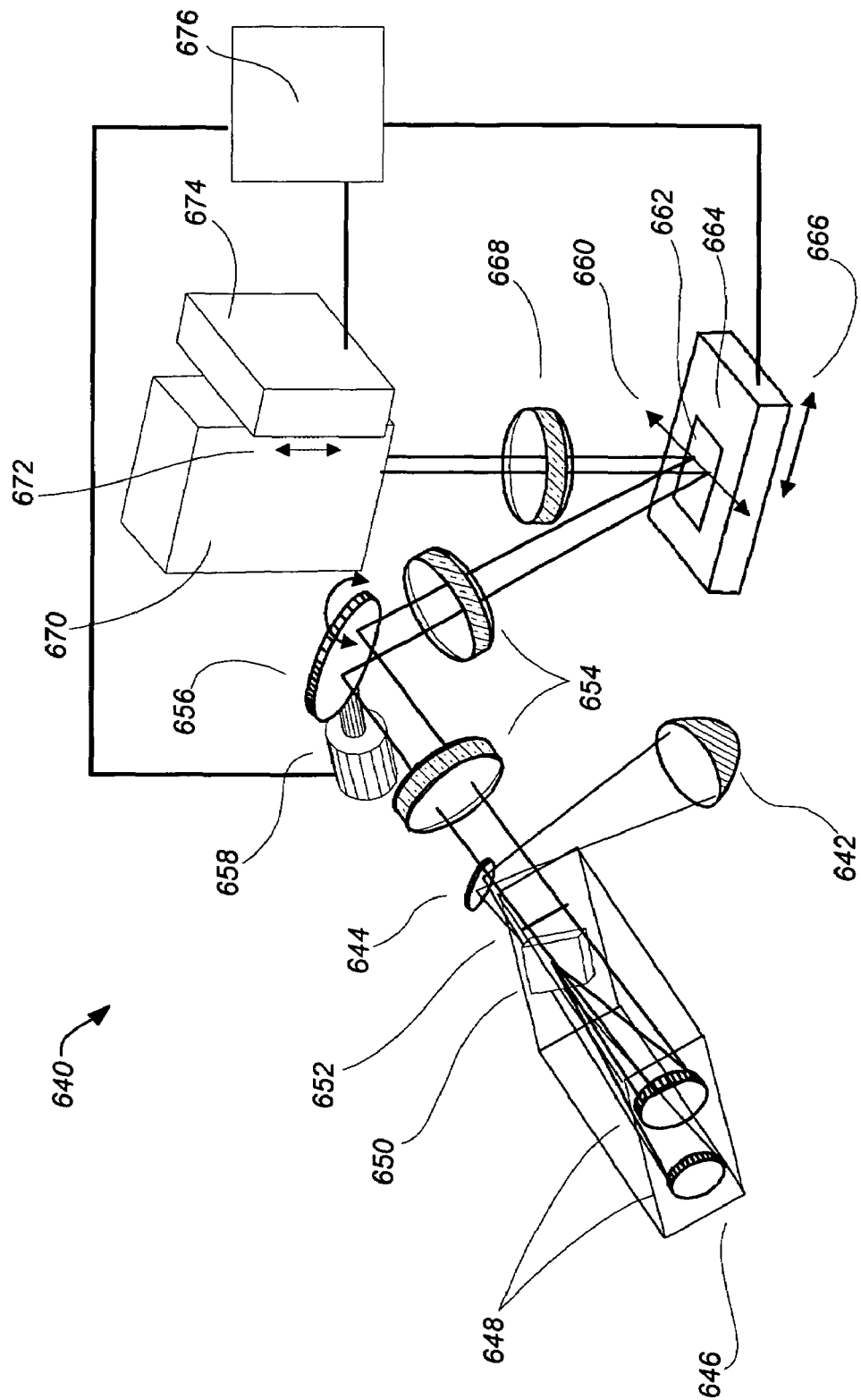
FIG. 6C is a system block diagram of an exemplary embodiment of the invention.

FIG. 6C is a system block diagram of an exemplary embodiment of the invention. The device 640 operates in a manner similar to the EEM imager 600 previously described in FIGS. 6A and 6B. The light source includes a lamp 642 which may be mounted within an ellipsoidal reflector to capture and direct the light. A turning mirror 644 is used to orient the light from the lamp 642 onto an entrance aperture of an excitation spectrograph 646. The excitation spectrograph 646 includes a variety of optics in light-sealed enclosure. The optics comprise collimating and refocusing mirrors 648. The refocusing mirror is oversized to accommodate the dispersion in wavelength. In addition, the optics of the excitation spectrograph 646 include a diffraction grating 650 oriented and tilted along an axis perpendicular to the usual orientation in a Czerny-Turner spectrometer to allow the excitation wavelength dispersion along the direction of the exit slit 652 (i.e. along the P axis). The excitation light exiting the excitation spectrograph 646 is focused through achromatic excitation relay lenses 654 bounding the scanning mirror 656. The scanning mirror 656 is moved about the indicated axis of rotation to scan the excitation light across the sample 662, passing an excitation stripe 660 across the sample 662 (along the M axis) in the direction of scanning. Movement of the scanning mirror 656 is controlled by the attached scanning mirror motor 658. The device 640 further comprises a translation stage 664 to move the sample 662 along a translation direction along the N axis 666, e.g. substantially perpendicular to the M axis.

As previously described, translation of the sample 662 along the N axis 666 may be performed after each completed scan. In this manner, the entire sample 662 is scanned in two dimensions. The emitted light from the sample 662 in response to the excitation is directed to one or more achromatic emission relay lenses 668 to direct the emitted light to an imaging spectrograph 670. The CCD detector 674 receives the emitted light having a wavelength dispersion within the imaging spectrograph 670 along the Q axis 672. A processor and motor control unit 676 comprises a data processor coupled to the two-dimensional detector 674 for controlling synchronization of the scanning mirror motor 658, translation stage 664 and receiving, storing and/or analyzing the derived excitation-emission matrix data. The processor and motor control unit 676 may comprises a computing device such as a personal computer (PC), a purpose-built digital processor or any other computing device capable of receiving and processing the excitation-emission matrix data from the detector 674. Typically, the computing device is a programmable computer which runs software adapted or programmed to receive and analyze the excitation-emission matrix data. In addition, the data processor may comprise a storage device such as a hard drive, optical drive or any other storage device for storing the received and/or processed excitation-emission matrix data from the detector 674. Analyzing the excitation-emission matrix data with the data processor may comprise a number of known techniques for identifying the species in the sample associated with the emission spectra.

In one novel process, the data processor can identify emission due to energy transfer between emitting species from the data of the excitation-emission matrix. The identification of energy transfer occurs because the energy from a donating species, or donor is the species which absorbs the excitation energy. Thus, the absorbance follows the spectral characteristics of the donor, but the energy accepting species, or acceptor, is the emitting species in this case, and hence the emission from the acceptor follows the spectral characteristic of the acceptor. Emission due to energy transfer exhibits a unique signature on an excitation-emission matrix, having the properties of the donor species along the excitation wavelength axis, but having the properties of the acceptor along the emission wavelength axis. Such a feature may be termed a cross peak, as its maximum occurs at the position of the maximum absorbance wavelength of the donor but at the maximum emission wavelength of the acceptor, and is hence distinct from the normal features of both the donor and acceptor on the excitation-emission matrix. This allows the ability to correct the quantification of amount of each emitting species present due to the effect of energy transfer, which would otherwise cause errors in such quantification in many circumstances.

Figure 7:
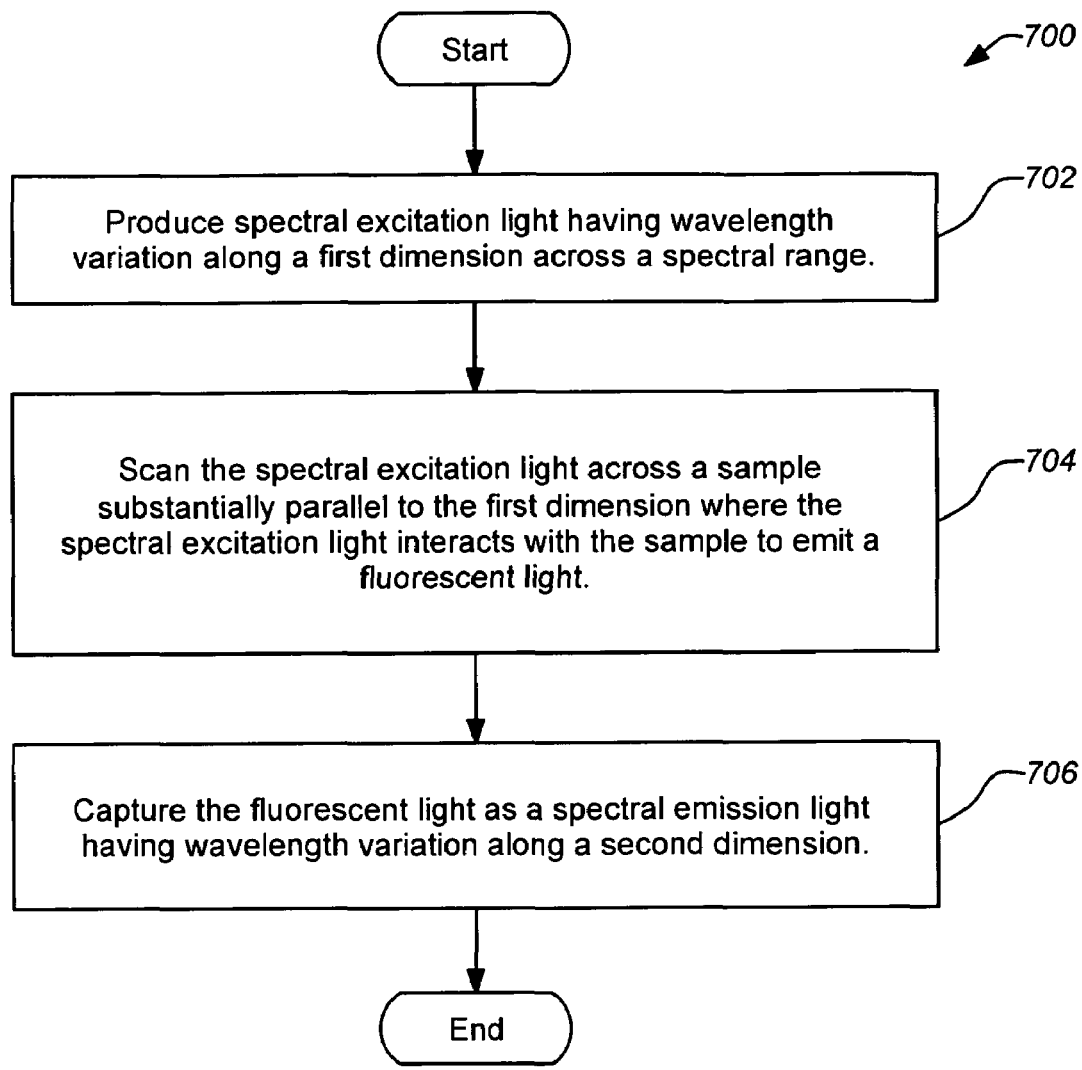
FIG. 7 is a flowchart of an exemplary method embodiment of the invention.

FIG. 7 is a flowchart of an exemplary method embodiment of the invention. The exemplary method 700 begins with an operation 702 of producing spectral excitation light having wavelength variation along a first dimension across a spectral range. Following this, an operation 704 of scanning the spectral excitation light across a sample substantially parallel to the first dimension is performed where the spectral excitation light interacts with the sample to cause secondary light emission, e.g., fluorescence. Finally, an operation 706 of capturing the emission light having wavelength variation along a second dimension is performed. Producing the spectral excitation light may be performed by repeating the spectral range along the first dimension such that scanning the spectral excitation light across the sample exhibits the spectral range to each point across the width of the sample. Furthermore, the sample may be moved in a second dimension distinct from the first dimension following each scan of the spectral excitation light across the sample.

Producing the spectral excitation light can be performed by producing and diffracting a broadband light and capturing the sample emission light can be performed by diffracting the fluorescent light along the second dimension. The scanning operation may be accomplished by reflecting the spectral excitation light and moving the reflected spectral excitation light across the sample substantially parallel to the first dimension. Alternately, scanning may be performed by moving the sample substantially parallel to the first dimension. In addition, the method 700 may be further modified consistent with the device embodiments previously detailed.

This concludes the description including the preferred embodiments of the present invention. The foregoing description of the preferred embodiment of the invention has been presented for the purposes of illustration and description. It is not intended to be exhaustive or to limit the invention to the precise form disclosed. Many modifications and variations are possible in light of the above teaching.

What is claimed is:

1. An apparatus, comprising:
   a light source for producing spectral excitation light having wavelength variation along a first dimension across a spectral range;
   a scanning device for scanning the spectral excitation light across a sample substantially parallel to the first dimension such that the wavelength variation across the spectral range of the spectral excitation light interacts with a spatial position along the sample to emit a secondary light; and
   an imaging device for capturing the secondary light as a spectral emission light having wavelength variation along a second dimension.

2. The apparatus of claim 1, wherein the sample comprises a width and the spectral excitation light comprises a repetition of the spectral range along the first dimension such that a single scan of the spectral excitation light across the sample exhibits the spectral range to each point across the width.

3. The apparatus of claim 1, wherein the sample comprises a two-dimensional array.

4. The apparatus of claim 1, wherein the light source comprises a lamp and a wavelength dispersion device.

5. The apparatus of claim 1, wherein the imaging device comprises an imaging spectrograph equipped with a two-dimensional detector.

6. The apparatus of claim 1, wherein the scanning device comprises a scanning mirror for reflecting the spectral excitation light and moving the reflected spectral excitation light across the sample substantially parallel to the first dimension.

7. The apparatus of claim 1, wherein the scanning device comprises a movable platform supporting the sample for moving the sample substantially parallel to the first dimension.

8. The apparatus of claim 1, further comprising a movable platform supporting the sample for moving the sample in a second dimension distinct from the first dimension following each scan of the spectral excitation light across the sample to repetitiously scan and capture the secondary light to produce an excitation-emission matrix for each spatial position on the sample.

9. The apparatus of claim 8, further comprising a data processor for identifying sample emission due to energy transfer between at least two emitting species from data of the excitation-emission matrix.

10. The apparatus of claim 9, wherein the data processor identifies a signature in the data of the excitation-emission matrix of a donor species and an acceptor species having the properties of the donor species along an excitation wavelength axis and the properties of the acceptor species along an emission wavelength axis.

11. The apparatus of claim 9, wherein the data processor corrects error in quantification of amount of the at least two emitting species due to the energy transfer between the at least two emitting species from the data of the excitation-emission matrix.

12. A method, comprising:
    producing spectral excitation light having wavelength variation along a first dimension across a spectral range;
    scanning the spectral excitation light across a sample substantially parallel to the first dimension such that the wavelength variation across the spectral range of the spectral excitation light interacts with a spatial position along the sample to emit a secondary light; and
    capturing the secondary light as a spectral emission light having wavelength variation along a second dimension.

13. The method of claim 12, wherein the sample comprises a width and producing the spectral excitation light comprises repeating the spectral range along the first dimension such that scanning the spectral excitation light across the sample exhibits the spectral range to each point across the width.

14. The method of claim 12, wherein the sample comprises a two-dimensional array.

15. The method of claim 12, wherein producing the spectral excitation light comprises producing and wavelength dispersing a broadband light.

16. The method of claim 12, wherein capturing the secondary light comprises wavelength dispersing the secondary light along the second dimension.

17. The method of claim 12, wherein scanning comprises reflecting the spectral excitation light and moving the reflected spectral excitation light across the sample substantially parallel to the first dimension.

18. The method of claim 12, wherein scanning comprises moving the sample substantially parallel to the first dimension.

19. The method of claim 12, further comprising repeating the scanning of the spectral excitation light across the sample and supporting and moving the sample in a second dimension distinct from the first dimension following each scan of the spectral excitation light across the sample and repeating the capturing of the secondary light to produce an excitation-emission matrix for each spatial position on the sample.

20. The method of claim 19, further comprising identifying sample emission due to energy transfer between at least two emitting species from data of the excitation-emission matrix.

21. The method of claim 20, further comprising identifying a signature in the data of the excitation-emission matrix of a donor species and an acceptor species having the properties of the donor species along an excitation wavelength axis and the properties of the acceptor species along an emission wavelength axis.

22. The method of claim 20, further comprising correcting error in quantification of amount of the at least two emitting species due to the energy transfer between the at least two emitting species from the data of the excitation-emission matrix.

23. An apparatus, comprising:
   means for producing spectral excitation light having wavelength variation along a first dimension across a spectral range;
   means for scanning the spectral excitation light across a sample substantially parallel to the first dimension such that the wavelength variation across the spectral range of the spectral excitation light interacts with a spatial position along the sample to emit a secondary light; and
   means for capturing the secondary light as a spectral emission light having wavelength variation along a second dimension.

* * * * *